United States Patent [19]

Sadjadi

[11] Patent Number: 5,480,354
[45] Date of Patent: Jan. 2, 1996

[54] SMART CROP YIELD MONITOR

[75] Inventor: Firooz A. Sadjadi, Minneapolis, Minn.

[73] Assignee: Loral Corporation, New York, N.Y.

[21] Appl. No.: 333,636

[22] Filed: Nov. 3, 1994

[51] Int. Cl.⁶ ..................................... A01F 12/50
[52] U.S. Cl. ............................ 460/7; 460/149; 56/10.2 B
[58] Field of Search ................................. 460/5, 1, 6, 7, 460/149; 56/10.2 B

[56] References Cited

U.S. PATENT DOCUMENTS

| | | | |
|---|---|---|---|
| 3,994,156 | 11/1976 | Koster | 73/76 |
| 4,052,666 | 10/1977 | Flotulou | 324/58.5 B |
| 4,327,521 | 5/1982 | Mason | 47/58 |
| 4,624,129 | 11/1986 | Haynes | 73/32 |
| 4,902,264 | 2/1990 | Diekhaus et al. | 460/5 |
| 4,929,904 | 5/1990 | Bohman | 324/696 |
| 5,092,819 | 3/1992 | Schroeder et al. | 460/7 |
| 5,106,339 | 4/1992 | Braun et al. | 460/7 |
| 5,309,374 | 5/1994 | Misra et al. | 364/552 |
| 5,312,299 | 5/1994 | Behnke et al. | 460/5 |
| 5,318,475 | 6/1994 | Schrock | 460/1 |
| 5,326,320 | 7/1994 | von Allwoerden | 460/149 |

Primary Examiner—Terry Lee Melius
Attorney, Agent, or Firm—Carl L. Johnson; Glenn W. Bowen

[57] ABSTRACT

An apparatus and method for on-the-go measuring of the amount and quality of grain being harvested including a first light source for projecting a first light image onto a pile of grain on a conveyor in a harvesting machine to cream a three-dimensional light image on the pile of grain on the conveyor and then converting the light image into coordinates for comparison to reference coordinates to determine the volume of the pile of grain on the conveyor belt; and an apparatus for determination of the amount of moisture in the pile of grain by projecting a second light image of a first wavelength onto the pile of grain, with the wavelength of the light of a frequency responsive to the amount of moisture in the pile of grain, and measuring the amount of reflectance of the light image of the first wavelength; and projecting a third light image of a second wavelength on the pile of grain, with the second wavelength of light in a region where reflectance is not responsive to the amount of moisture in the pile of grain, measuring the amount of reflectance of the light image of the second wavelength comparing the ratio of reflectance of the light image of the first wavelength to the reflectance of the light image of the second wavelength to determine the amount of moisture in the pile of grain and location-measuring equipment for determining an area of standing crop harvested.

7 Claims, 2 Drawing Sheets

SMART CROP YIELD MONITOR

FIELD OF THE INVENTION

The invention relates generally to grain-monitoring equipment for placement on grain-harvesting and, more specifically, to on-the-go grain-monitoring equipment determining the volume and the moisture content of a harvested grain during the harvesting process.

BACKGROUND OF THE INVENTION

One of the important measurements a farmer makes is the yield measurement of his or her crops. Yield is usually expressed in bushels per acre; however, not only is the amount of grain obtaining from a given area important, it is also important to know yield-related information such as the moisture content of the harvested grain. Generally, high-moisture grains must be dried before storage or must be sold at a discount to cover drying costs of the purchaser. Farmers' profits relate directly to yield, so the sooner a farmer obtains yield-related information, the sooner the farmer improves his or her evaluation of the field factors which affect yield. Numerous methods have been employed to measure the yield of harvested crops during the harvesting process. The present invention provides a simple, low-cost method of using off-the-shelf items to determine the moisture content and the volume of the harvested crop. Coupling the present invention with an area-computation system facilitates determination of the yield of the crop per given acre together with the moisture content during harvesting of the crop

DESCRIPTION OF THE PRIOR ART

U.S. Pat. No. 5,318,475 shows an apparatus for measuring mass flow of grain including a weighing station to weigh the grain.

U.S. Pat. No. 4,624,129 shows a device for measuring the density of a dry product using acoustic impedance.

U.S. Pat. No. 4,929,904 shows a moisture sensor using probes that are inserted into the crop and measuring the conductance level between the probes.

U.S. Pat. No. 3,994,156 shows a device for measuring the moisture of a crop by blowing air over the crop and measuring the weight loss of the crop.

U.S. Pat. No. 5,326,320 shows a method and apparatus for accelerating the drying process by pressing the material.

U.S. Pat. No. 4,052,666 shows an apparatus for remote sensing of vegetation moisture by use of reflected polarized light.

U.S. Pat. No. 4,327,521 shows method of increasing the growth of hedge-row plants by cutting the plants so the sun impinges more directly.

U.S. Pat. No. 5,309,374 shows use of acoustic and video signal processing to determine the mass, hardness or other quality feature of the product.

SUMMARY OF THE INVENTION

The invention comprises an apparatus and method for on-the-go measuring of the amount and quality of grain being harvested as well as the yield of the harvest. The system includes a first light source for projecting a first light image onto grain located on a conveyor in a harvesting machine to create a three-dimensional light image on the top surface of the grain. A camera and processor convert the light image into coordinates for comparison to reference coordinates to determine the volume of grain on the conveyor belt. The system further includes an apparatus for determination of the moisture content of the grain. The apparatus uses a light source which emits a first wavelength of light at a frequency which is responsive to the amount of moisture in the grain and a second wavelength at a frequency which is unresponsive to the amount of moisture in the grain. A camera and processor measures the amount of reflectance of the light image of the first wavelength, the amount of reflectance of the light image of the second wavelength, and then compares the ratio of reflectance of the light image of the first wavelength to the reflectance of the light image to stored information on reflectance ratios of identical wavelengths which were computed from graphs of actual moisture in a crop to enable one to determine the amount of moisture in the harvested grain. The system further includes location-measuring equipment for determining an area of standing crop harvested and relating that area to the volume and the moisture content of the crop which provides an on-the-go yield of the harvested crop.

DESCRIPTION OF THE PREFERRED EMBODIMENT

Figure 1:
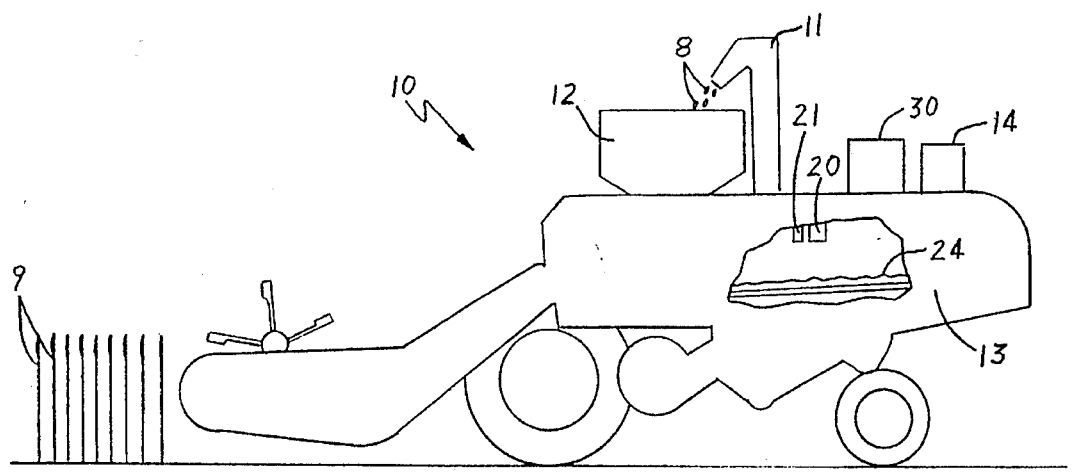
FIG. 1 shows a combine harvesting standing grain.

FIG. 1 shows a combine 10 harvesting a standing crop 9 of grain. Combine 10 includes a global-position sensor 30 for determining the movement of the combine, a chute 11 for delivering the harvested grain kernels 8 to a bin 12. The side of the combine 10 is a partial cut-away view to show a system 13 for measuring the volume and moisture of a pile of grain 24 carried by conveyor 23. The global-position sensor 30 provides information on the area of grain harvested by determining the movement of the combine. An on-board computer 14 provides the capability of converting information to actual volume- and moisture-content of the crop.

Figure 2:
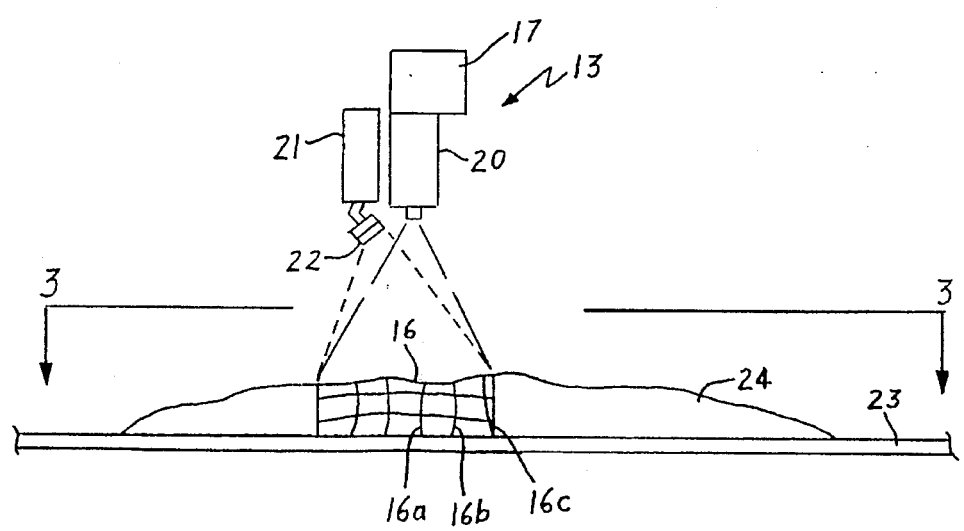
FIG. 2 shows a partial cut-away side view showing the system of the present invention together with a conveyor moving a pile of grain.

FIG. 2 shows further details of system 13 with a halogen light source 21 for projecting a light image 16 in the lbrm of a rectangular grid having grid lines identified by 16a, 16b, 16c and so on on the top surface of a pile of grain 24 located on conveyor 23. Located in front of halogen light source 21 is a filter for selectively transmitting light of a single wavelength.

Figure 3:
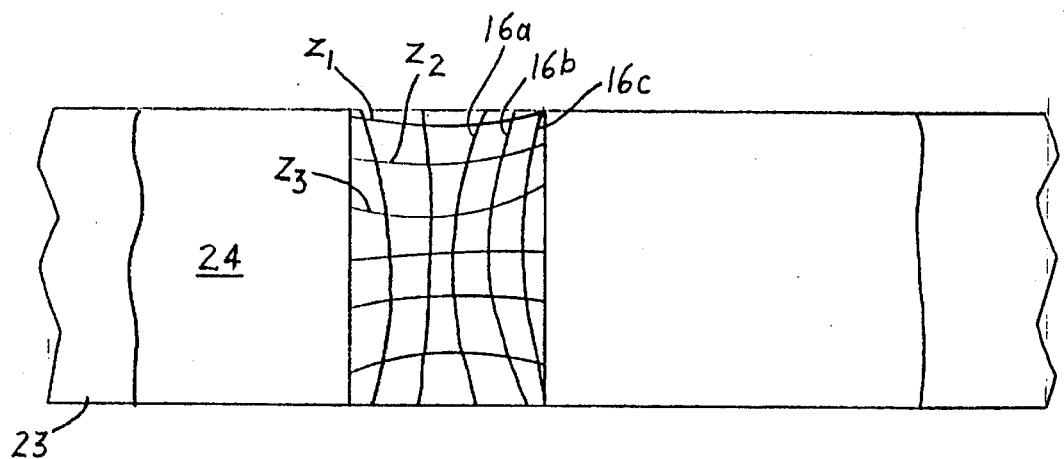
FIG. 3 is to view taken along lines 3—3 of FIG. 2.

FIG. 3 shows a top view taken along lines 3—3 of FIG. 2 showing conveyor 23 with a pile of grain 24 thereon. Light grid 16 is shown located on the top surface of grain 24 with the projected rectangular light grid distorted in accordance with the shape of the pile of grain.

Figure 4:
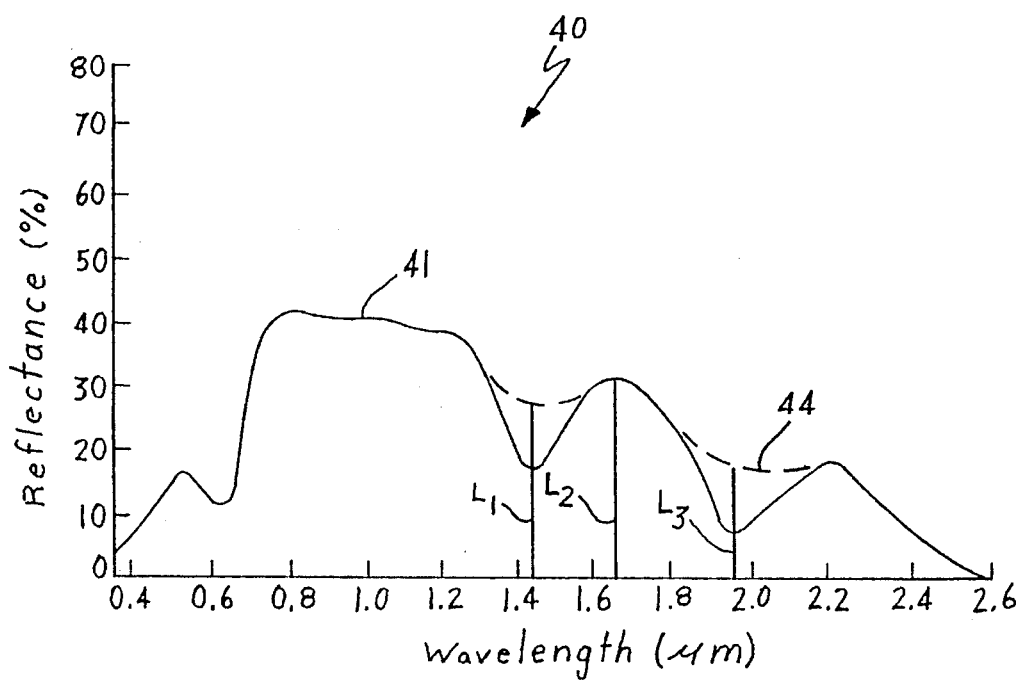
FIG. 4 is a graph of the reflectance of a crop to light of different wavelengths.

FIG. 4 is a graph of the reflectance of various wavelengths for a harvested crop having a particular moisture content identified by line 41. The vertical axis denotes light reflectance in percentage, and the horizontal axis denotes the particular wavelength. The graph shows how the light reflectance varies with changes in wavelength. In this graph, there are three significant and distinct wavelengths that are either at peaks or valleys in the graph. These valley wavelengths are identified by $L_1$ and $L_3$. The valley wavelengths show that, for grain of a particular moisture content, the light reflectances from the grain are weakly reflected (about 15 to 20 percent.) These two valleys correspond to two wavelengths where the amount of water in the grain has a substantial effect on the light reflection; that is, at wavelengths $L_1$ and $L_3$, the grain absorbs the light and limits the amount of reflectance. On the other hand, the light wavelength $L_2$ corresponds to a frequency where the light reflected is substantially independent of the water content of the crop (about 30 percent reflectance) A second dashed line 44 corresponds to the reflectance characteristics of grain of a different moisture content. Note that the reflectance at wavelength $L_2$ remains the same, but the reflectance at wavelengths $L_1$ and $L_3$ increases. In other words, at the two wavelengths $L_1$ and $L_3$, the amount of light reflectance is responsive to the amount of moisture in the grain, and at wavelength $L_2$ the reflectance of light is unresponsive to the amount of moisture in the grain. This information, coupled with various family of curves of reflectance with moisture content of a crop, allows one to determine the moisture content of the grain by knowing the ratio of the reflectance at the particular wavelengths $L_1/L_2$ or $L_2/L_3$.

In the embodiment shown in FIG. 1, grid 16 comprises dark lines with illuminated areas between the dark lines of the grid. However, grid 16 could comprise light lines with non-illuminated areas between grid lines 16. The preferred source of light is a halogen bulb, as it is readily available and emits visible light over a broad range which extends to the near infrared range. Located proximate to light source 21 is a video camera 20 for obtaining an optical image of the grid pattern 16. Because the grid pattern follows the surface of the pile of grain, the camera provides an image of the grid with the lines closer to the camera appearing to the camera as having greater intensity and the lines farther from the camera appearing as having less intensity. For each intersection of the grid, there are spatial coordinates with the height of the grain at each intersection being designated by z. For example, FIG. 3 shows points identified by $z_1$, $z_2$, $z_3$ and so on. Video camera 20 transmits the optical image to a processor 17 which converts the optical image into three dimensional coordinates; i. e., x, y, z where they are compared to the three-dimensional coordinates of conveyor 23 without grain 24 thereon. By knowing the difference in coordinates between the conveyor with grain or no grain, the processor determines the volume of grain passing through the combine.

To obtain information on the moisture content of grain, a filter is placed over light source 21 so that light of only a wavelength $L_1$ is projected onto grain 24. The camera 20 receives the image of wavelength $L_1$, and a processor 17 converts the optical image into a light-reflectance value. Next, a second filter is placed over light source 22 so that only light of a wavelength $L_2$ is projected onto grain 24. The camera 20 also receives the image of wavelength $L_2$, and a processor 17 converts the optical image into a light-reflectance value. By projecting a light image of a first wavelength $L_1$ that is responsive to the amount of moisture in the pile of grain and a second wavelength $L_2$ that is not responsive to the amount of moisture in the grain and than measuring the amount of reflectance of the light image at wavelength $L_2$ and at wavelength $L_1$, one can determine a ratio of reflectance which is dependent of the moisture in the grain.

Comparing the measured ratio of reflectance of the light image of the first wavelength to the reflectance of the light image of the second wavelength enables ready determination of the amount of moisture in the grain by reference to measured ratios where the actual moisture content of the grain is known.

To determine the yield on a per-unit basis, one obtains information on the position of the combine from global-position sensor 30 and correlates it with the volume of grain passing through the conveyer to give an on-the-go yield, typically in bushels per acre. The moisture content obtained from the reflectance and the yield are displayed on computer 14 to provide the operator with continuing and current information on yield and yield-related information of the harvested crop.

I claim:

1. A method of measuring the volume of grain harvested from a standing crop while the standing crop is continuing to be harvested comprising the steps of:

projecting a light image onto a pile of grain on a conveyor in a harvesting machine to create a three-dimensional light image on the pile of grain on the conveyor;

viewing the light image;

converting the light image into coordinates for comparison to reference coordinates for determining the volume of the pile of grain on the conveyor belt projecting a second light image of a first wavelength onto the pile of grain, with the wavelength of the light of a frequency that is responsive to the amount of moisture in the pile of grain;

measuring the amount of reflectance of the light image of the first wavelength;

projecting a third light image of a second wavelength onto the pile of grain with the second wavelength of light of a frequency is not responsive to the amount of moisture in the pile of grain;

measuring the amount of reflectance of the light image of the second wavelength; and comparing the ratio of reflectance of the light image of the first wavelength to the reflectance of the light image of the second wavelength to determine the amount of moisture in the pile of grain.

2. The method of claim 1 for on-the-go yield measurement of the standing crop including the steps of:

measuring an area of standing crop harvested; and relating the area of standing crop harvested to the volume and moisture content of the crop to obtain an on-the-go yield of the crop.

3. The method of claim 1 for on-the-go yield measurement of the standing crop including the steps of:

measuring an area of standing crop harvested; and relating the area of standing crop harvested to the volume of the crop to obtain an on-the-go yield of the crop.

4. The method of claim 1 wherein the first light image is projected on in a grid pattern.

5. The method of claim 1 wherein the first wavelength and second wavelength are in an infrared region of the spectrum.

6. An apparatus for measuring the volume of grain harvested from a standing crop while the standing crop is continuing to be harvested comprising:

a conveyor for moving a harvested grain crop from a first position to a second position with the conveyor carrying a pile of grain thereon;

a light source for projecting a light image onto the pile of grain;

a light-measuring means for measuring the intensity of the light image at various points on the light image;

a processor for converting the light measurements into three-dimensional coordinates and for determining the volume of the harvested grain crop by using the three-dimensional coordinates of the pile of grain;

a light source for projecting a second light image of a first wavelength onto the pile of grain, with the wavelength of the light of a frequency that is responsive to the amount of moisture in the pile of grain;

a means for measuring the amount of reflectance of the light image of the first wavelength;

the light source projecting a third light image of a second wavelength onto the pile of grain, with the second wavelength of light in a region where water is not responsive to the amount of moisture in the pile grain;

a means for measuring the amount of reflectance of the light image of the second wavelength; and a processing means for comparing the ratio of reflectance of the light image of the first wavelength to the reflectance of the light image of the second wavelength to determine the amount of moisture in the pile of grain.

7. The method of determining the amount of moisture in the pile of grain located in a harvesting machine comprising the steps of:

projecting a light image of a first wavelength onto the pile of grain with the wavelength of the light of a frequency that is responsive to the amount of moisture in the pile of grain;

measuring the amount of reflectance of the light image of the first wavelength;

projecting a second light image of a second wavelength onto the pile of grain with the second wavelength of light of a frequency that is not responsive to the amount of moisture in the pile of grain;

measuring the amount of reflectance of the light image of the second wavelength; and comparing the ratio of reflectance of the light image of the first wavelength to the reflectance of the light image of the second wavelength to determine the amount of moisture in the pile of grain.

* * * * *